United States Patent [19]
Holick et al.

[11] Patent Number: 4,521,410
[45] Date of Patent: Jun. 4, 1985

[54] VITAMIN D GLYCOSYL ORTHOESTERS

[75] Inventors: Michael F. Holick; Sally A. Holick, both of Sudbury, Mass.

[73] Assignee: The General Hospital Corporation, Boston, Mass.

[21] Appl. No.: 607,117

[22] Filed: May 3, 1984

[51] Int. Cl.³ .................... A01N 31/00; A61K 31/70
[52] U.S. Cl. .................... 514/26; 536/18.1; 260/397.2; 514/169
[58] Field of Search ............ 424/180, 236; 536/18.1; 260/397.2

[56] References Cited
U.S. PATENT DOCUMENTS
4,410,515 10/1983 Holick et al. .................... 536/4.1

OTHER PUBLICATIONS

Hughes, M. R. et al., Nature, 268: 347–349, (1977).
Peterlik, M. et al., FEBS Letters, 56: 16–19, (1973).
Humphreys, D. J., Nature (London) New Biology, 246: 155–157, (1973).
Peterlik, M. et al., Biochemical and Biophysical Research Communications, 70: 797–803, (1976).
Furst, A. et al., Helvetica Chimica Acta, 66: 2093–2102, (1983).
Haussler, M. R., Life Sciences, 18: 1049–1054, (1976).
Wasserman, R. H., Science, 194: 853–855, (1976).
Napoli, J. L. et al., The Journal of Biological Chemistry, 252: 2580–2583, (1977).

Primary Examiner—Elbert L. Roberts
Attorney, Agent, or Firm—Saidman, Sterne, Kessler & Goldstein

[57] ABSTRACT

A compound which is biologically active in maintaining calcium and phosphorous metabolism in animals, selected from the group consisting of formula (IA) and (IB):

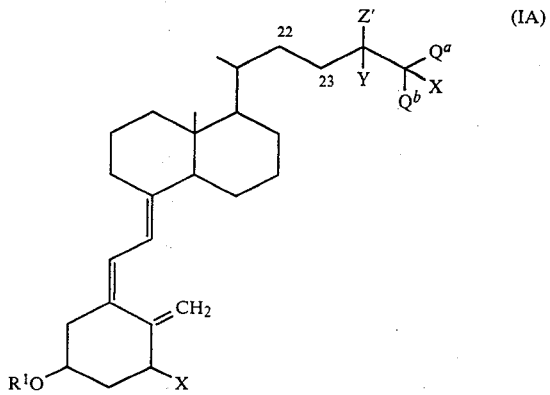

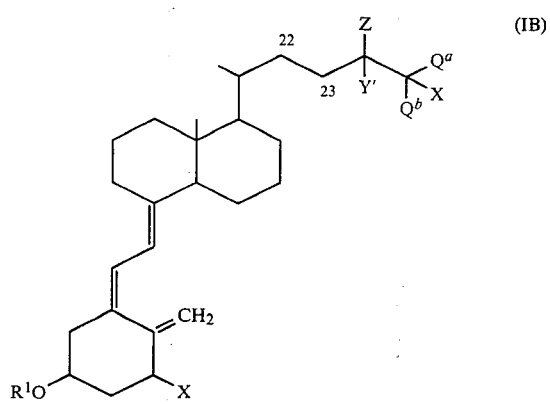

wherein the bond between carbons C-22 and C-23 is single or double; Y is hydrogen, F, —CH₃ or —CH₂CH₃; Z is F, H or X; Y' is H, —CH₃ or —CH₂CH₃; Z' is F or H; $Q^a$ is CF₃ or CH₂X; $Q^b$ is CF₃ or CH₃; X is selected from the group consisting of hydrogen and —OR¹, wherein R¹ is hydrogen or an orthoester glycoside radical of the formula (II)

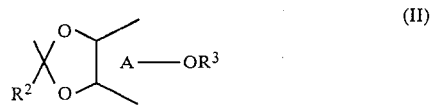

where A represents a glucofuranosyl or glucopyranosyl ring; R² is hydrogen, lower alkyl, aralkyl, or aryl; and R³ is hydrogen or a straight or branched chain glycosidic residue containing 1–100 glycosidic units per residue; with the proviso that at least one of the R¹ is an orthoester glycoside moiety of formula (II).

29 Claims, No Drawings

VITAMIN D GLYCOSYL ORTHOESTERS

BACKGROUND OF THE INVENTION

1. Field of the Invention

The present invention relates to water-soluble synthetic glycosyl orthoesters of vitamin D, and their use in the regulation of calcium metabolism.

2. Description of the Background Art

Vitamin $D_3$ deficiency, or disturbances in the metabolism of vitamin $D_3$ cause such diseases as rickets, renal osteodystrophy and related bone diseases, as well as, generally, hypo- and hyper-calcemic states. Vitamin $D_3$ and its metabolites are therefore crucial in maintaining normal development of bone structure by regulating blood calcium levels.

Vitamin $D_3$ is rapidly converted to 25-OH-$D_3$ in the liver. In response to hypocalcemia, 25-OH-$D_3$, the major circulating metabolite of the vitamin, undergoes further metabolism in the kidney to 1,25-$(OH)_2D_3$. 1,25-$(OH)_2D_3$ acts more rapidly than either $D_3$, or 25-OH-$D_3$. Additionally, the dihydroxy form of the vitamin is 5–10 times more potent than $D_3$, and about 2–5 times more potent than the monohydroxy form of the vitamin, in vivo, provided it is dosed parenterally and daily (Napoli, J. L. and Deluca, H. F., "Blood Calcium Regulators" and references cited therein in: *Burger's Medicinal Chemistry*, 4th Ed., part II, edited by Manfred Wolf, Wiley-Interscience, 1979, pp. 725–739).

Vitamin $D_2$, vitamin $D_3$ or their metabolites which are hydroxylated at positions 1; 1,25; 1,24,25; 24,25; 25,26; or 1,25,26 are water-insoluble compounds. When a drug is relatively insoluble in an aqueous environment or in the gastrointestinal lumen, post-administration dissolution may become the rate-limiting step in drug absorption. On the other hand, with water-soluble drugs, dissolution occurs rapidly and thus facilitates transport through blood and to the site of activity. It would therefore be desirable to provide a form of vitamin D ($D_3$ or $D_2$) which is hydrophilic and/or water-soluble, yet preserves the normal biological properties of the water-insoluble drug.

The extracts from the leaves of a South American plant, *Solanum malacoxylon* (hereinafter "*S.m.*"), have been demonstrated to contain a water-soluble principle which is different than 1,25$(OH)_2D_3$ and which, upon treatment with glycosidase enzymes yields 1,25$(OH)_2D_3$, plus a water-soluble unidentified fragment. (See, for example, Haussler, M. R., et al., Life Sciences, Volume 18: 1049–1056 (1976); Wasserman, R. H., et al., Science 194: 853–855 (1976); Napoli, J. L., et al., *The Journal of Biological Chemistry*, 252: 2580–2583 (1977)).

A very similar water-soluble principle, which upon treatment with glycosidases also yields 1,25-dihydroxy vitamin $D_3$, is found in the plant *Cestrum diurnum* (hereinafter "*C.d.*"); Hughes, M. R., et al., *Nature*, 268: 347–349 (1977)). The water soluble extracts for *S.m.* or *C.d.* have biological activity which is similar to that of 1,25-dihydroxy vitamin $D_3$.

The only evidence concerning the structure of the water-soluble fragment released during glycosidase treatment of the water-soluble principles from these plants is indefinite. The authors of the aforementioned publications have concluded that the structure is probably a glycoside, on the basis of enzymatic evidence, the water-solubility, and the use of chemical detection reagents (Peterlik, N. and Wasserman, R. H., *FEBS Lett.* 56: 16–19 (1973)). Humphreys (*Nature* (London) *New Biology* 246: 155 (1973)), however, has cast some doubt on this conclusion since he demonstrated that the Molisch carbohydrate test was negative for the principle.

Since it is known that the molecular weight of the water-soluble vitamin $D_3$-containing principle, prior to enzymatic release, is considerably greater than 1000 (Humphreys, D. J., *Nature* (London) *New Biology* 246: 155 (1973)), the molecular weight of the water-soluble conjugated fragment released by enzymatic hydrolysis can be calculated to be considerably greater than 584, the molecular weight of dihydroxy vitamin $D_3$ being 416. Thus, if the water-soluble fragment released by enzymatic hydrolysis were in fact a glycoside, it would contain more than 3 glycosidic (glycopyranosyl or glycofuranosyl) units.

Moreover, the results of enzymatic release are fully consistent with a wide variety of structures. For example, Haussler, M. R., et al., *Life Sciences* 18: 1049–1056 (1976) disclose the use of mixed glycosidases derived from *Charonia lampus* to hydrolyze the water-soluble principle. This enzyme is really a mixture of enzymes, as follows (Miles Laboratories, 1977 catalog): $\beta$-glucosidase (11 units), $\alpha$-mannosidase (33 units), $\beta$-mannosidase (5.2 units), $\alpha$-glucosidase (4.8 units), $\beta$-galactosidase (44 units), $\alpha$-galactosidase (26 units), $\alpha$-fucosidase (24 units), $\beta$-xylosidase (8.2 units), $\beta$-N-acetylglucosaminidase (210 units), $\alpha$-N-acetylgalactosaminidase (41 units), and $\beta$-N-acetyl-galactosaminidase (25 units). Peterlik, M., et al. (*Biochemical and Biophysical Research Communications*, 70: 797–804 (1976)) in their study of the *S.m.* extract with $\beta$-glucosidase (almond) from Sigma Chemical Company, utilized an enzyme that also contained $\beta$-D-galactosidase, and $\alpha$-D-mannosidase activities (Sigma Chemical Company, February 1981 Catalog; see also, Schwartz, J., et al., *Archives of Biochemistry and Biophysics*, 137: 122–127 (1970)).

In sum, the results observed by these authors are consistent with a wide range of structures, none of which have been well characterized but which, even if proven to be glycosides, contain at least more than 3 glycosidic units per vitamin D unit.

Holick, et al., U.S. Pat. No. 4,410,515 describe water-soluble glycoside derivatives of Vitamin D which are biologically active. Furst, et al., *Helv. Chim. Acta*, 66: 2093 (1983) have also synthesized Vitamin D glycopyranosyl derivatives.

A need, however, continues to exist for other well-defined, well-characterized water-soluble forms of vitamin D, which will be hypocalcemically active and maintain calcium and phosphorus homeostasis.

SUMMARY OF THE INVENTION

The present invention thus provides:

A synthetic compound which is biologically active in maintaining calcium and phosphorous homeostasis in animals, selected from the group consisting of formula (IA) and (IB):

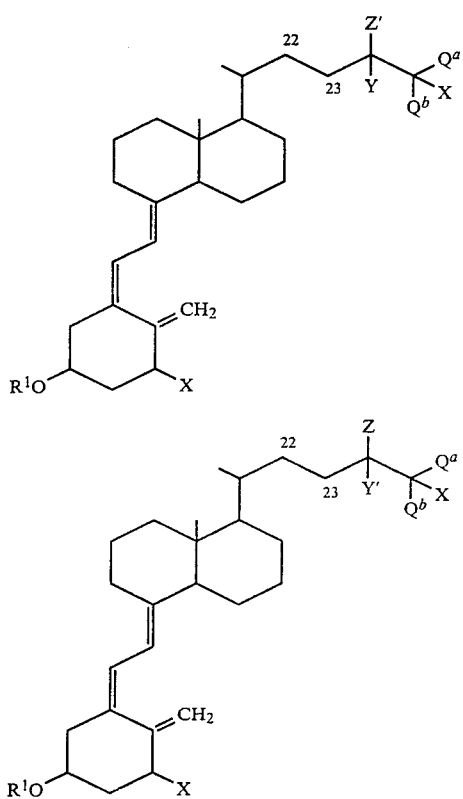

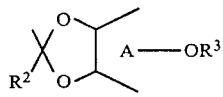

wherein the bond between carbons C-22 and C-23 is single or double;
Y is hydrogen, F, —CH$_3$ or —CH$_2$CH$_3$;
Z is F, H or X;
Y' is H, —CH$_3$ or —CH$_2$CH$_3$;
Z' is F or H;
Q$^a$ is CF$_3$ or CH$_2$X;
Q$^b$ is CF$_3$ or CH$_3$;
wherein X is selected from the group consisting of hydrogen and —OR$^1$, where —R$^1$ is hydrogen or an orthoester glycoside moiety of the formula (II)

(II)

where A represents a glucofuranosyl or glucopyranosyl ring; R$^2$ is hydrogen, lower alkyl, aralkyl, or aryl (including both endo and exo isomers); and R$^3$ is hydrogen or a straight or branched chain glycosidic residue containing 1–100, especially 1–20 glycosidic units per residue;
with the proviso that at least one of said R$^1$ is an orthoester glycoside moiety of formula (II).

DESCRIPTION OF THE PREFERRED EMBODIMENTS

The present invention provides well-defined water-soluble forms of vitamin D$_3$ and D$_2$, as well as hydroxylated derivatives of these vitamins. The compounds of the present invention may in many instances be crystalline.

By glycosidic units are meant glycopyranosyl or glycofuranosyl, as well as their amino sugar derivatives. The residues may be homopolymers, random, or alternating or block copolymers thereof. The glycosidic units have free hydroxy groups, or hydroxy groups acylated with a group $$R^2-\underset{\underset{O}{\|}}{C}-,$$

wherein R$^2$ is hydrogen, lower alkyl, aryl or aralkyl. Preferably R$^2$, as defined previously, is C$_1$-C$_6$ alkyl, most preferably acetyl or propionyl; phenyl, nitrophenyl, halophenyl, lower alkyl-substituted phenyl, lower alkoxy substituted phenyl, and the like; or benzyl, nitrobenzyl, halobenzyl, lower alkyl-substituted benzyl, lower alkoxy-substituted benzyl, and the like.

When the compounds of formula (I) have a double bond at position C-22, they are derivatives of vitamin D$_2$; whereas, if the bond at that position is single, and there is a lack of a C$_{24}$ alkyl they are derivatives of vitamin D$_3$. The latter are preferred.

The compounds of the invention contain at least one orthoester glycoside moiety of formula (II) at positions 1, 3, 24, 25 or 26. They may, however, contain more than one, and up to five such radicals simultaneously. The orthoester moiety of formula (II) may comprise a glucofuranosyl moiety or a glucopyranosyl moiety in its first unit.

A glucopyranosyl moiety results in an orthoester moiety of formulae (III), (IV) or (V):

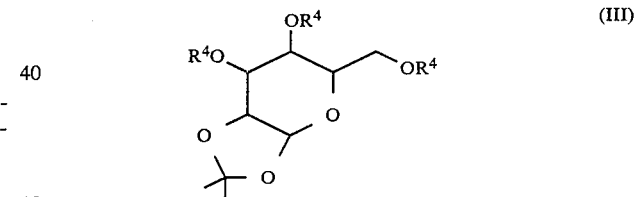

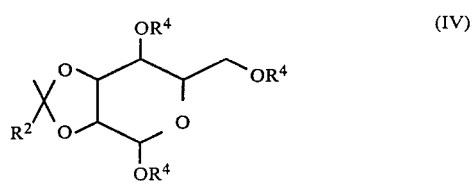

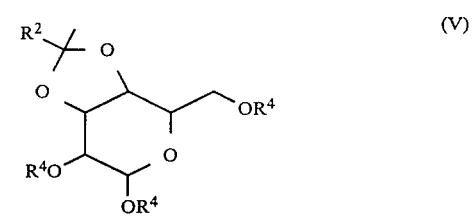

where R$^4$ is R$^2$ or R$^3$, and where R$^2$ and R$^3$ have the meanings given above.

A glucofuranosyl moiety results in an orthoester radical of formulae (VI) or (VII):

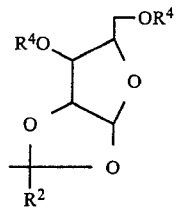

(VI)

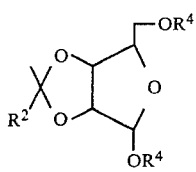

(VII)

where $R^4$ is $R^2$ or $R^3$, and $R^2$ and $R^3$ have the meanings given above.

Preferred are those compounds derived from vitamins $D_3$ or $D_2$; 1-hydroxy-vitamins $D_3$ or $D_2$; 1,25-dihydroxy vitamins $D_3$ or $D_2$; 24,25-dihydroxy vitamins $D_3$ or $D_2$; 25,26-dihydroxy vitamins $D_3$ or $D_2$; 1,24,25-trihydroxy vitamins $D_3$, or $D_2$. Most preferred among these are vitamins $D_3$ or $D_2$; 1-hydroxy-vitamins $D_3$ or $D_2$; and 1,25-dihydroxy-vitamins $D_3$ or $D_2$.

In the case of multihydroxylated forms of the vitamins (e.g.: 1,25-dihydroxy-vitamin $D_3$ has three hydroxy groups, at positions 1, 3 and 25), the preferred compounds of the invention are those wherein less than all of the multiple hydroxy groups are substituted with a radical of formula (II).

The glycoside residues $R^3$ can comprise up to 100, especially up to 20 glycosidic units. Preferred, however, are those having less than 10, most preferred, those having 3 or less than 3 glycosidic units. Specific examples are those containing 1 or 2 glycosidic units in the glycoside residue $R^3$.

The glycopyranose or glycofuranose rings or amino derivatives thereof, whether part of the moiety of formula (II) or part of the glycosidic residue $R^3$, may be fully or partially acylated or completely deacylated. The completely or partially acylated glycosyl orthoesters are useful as intermediates for the synthesis of the deacylated materials.

Among the possible glycopyranosyl structures useful in $R^3$ are glucose, mannose, galactose, gulose, allose, altrose, idose, or talose. Among the glycofuranosyl structures useful in $R^3$, the preferred ones are those derived from fructose, or arabinose. Among preferred diglycosides are sucrose, cellobiose, maltose, lactose, trehalose, gentiobiose, and melibiose. Among the triglycosides, the preferred ones may be raffinose or gentianose. Among the amino derivatives are N-acetyl-D-galactosamine, N-acetyl-D-glucosamine, N-acetyl-D-mannosamine, N-acetylneuraminic acid, D-glucosamine, lyxosylamine, D-galactosamine, and the like.

Among the possible glycopyranosyl structures useful in moiety (II) are glucose, galactose or gulose. Among the glycofuranosyl structures useful in moiety (II) are those derived from arabinose. Diglycosides useful in moiety (II) include cellobiose, maltose, lactose, gentiobiose and meliobiose. Among the triglycosides useful in moiety (II) are maltotriose, cellotriose, and panose. An example of an amino derivative is 3-amino-3,6-dideoxy-D-galactose.

When more than one glycosidic unit per $R^3$ is present on a single hydroxy group (i.e., di or polyglycosidic residues), the individual glycosidic rings may be bonded by 1-1, 1-2, 1-3, 1-4, 1-5 or 1-6 bonds, most preferably 1-2, 1-4, and 1-6. The linkages between individual glycosidic rings may be alpha or beta.

The configuration of the oxygen linkage of a hydroxy group, or orthoester glycoside moiety (II) attached to the Vitamin $D_3$ or $D_2$ molecule may be either alpha (out of the plane of the paper) or beta (into the plane of the paper). It is preferred if the configuration of the 3-hydroxy or orthoester glycoside moiety (II) at C-3 be beta, and that, independently or simultaneously, the configuration of the hydroxy or orthoester glycoside moiety (II) at C-1 be alpha. It is also preferred that the configuration around C-24 be R. When, at C-24, X=H and $R^2$=—$CH_3$ or —$CH_2CH_3$, the configuration at C-24 is preferably S.

In one embodiment, the carbon at position 24 of the Vitamin D moiety may be substituted by two F atoms. In another embodiment, the 26 and 27 methyl groups of the Vitamin D moiety are replaced by $CF_3$ groups, and X at position 25 is an $OR^1$ group.

Specific examples of compounds of the invention are:

1α-(α-D-maltosyl-1′,2′-orthoacetate)-Vitamin $D_3$;
1α-(α-D-lactosyl-1′,2′-orthoacetate)-Vitamin $D_3$;
1α-(α-D-gentiobiosyl-1′,2′-orthoacetate)-Vitamin $D_3$;
1α,25-dihydroxyvitamin $D_3$, 3β-(a-D-glycopyranosyl-1′,2′-orthoacetate);
1α,25-dihydroxy-26,27-hexafluorovitamin $D_3$, 3β-(α-D-glucopyranosyl-1′,2′-orthoacetate);
1α,25-dihydroxy-24,24-difluoro Vitamin $D_3$, 3β-(α-D-glucopyranosyl-1′,2′-orthoacetate);
1α-(α-D-glucopyranosyl-1′,2′-orthoacetate)-25-hydroxy-Vitamin $D_3$;
1α-hydroxy, 25-(α-D-cellobiosyl-1′,2′-orthoacetate)-Vitamin $D_3$;
1α-hydroxy, 25-(α-D-maltosyl-1′,2′-orthoacetate)-Vitamin $D_3$;
1α-hydroxy, 25-(α-D-lactosyl-1′,2′-orthoacetate)-Vitamin $D_3$;
1α-hydroxy, 25-(α-D-gentiobiosyl-1′,2′-orthoacetate)-Vitamin $D_3$;
Vitamin $D_3$, α-D-glucopyranosyl-1′,2′-orthoacetate;
Vitamin $D_3$, α-D-cellobiosyl-1′,2′-orthoacetate;
Vitamin $D_3$, α-D-maltosyl-1′,2′-orthoacetate;
Vitamin $D_3$, α-D-lactosyl-1′,2′-orthoacetate;
Vitamin $D_3$, α-D-gentiobiosyl-1′,2′-orthoacetate;
1α-hydroxyvitamin $D_3$, 3β-(α-D-glucopyranosyl-1′,2′-orthoacetate);
1α-hydroxyvitamin $D_3$, 3β-(α-D-cellobiosyl-1′,2′-orthoacetate);
1α-hydroxyvitamin $D_3$, 3β-(α-D-maltosyl-1′,2′-orthoacetate);
1α-hydroxyvitamin $D_3$, 3β-(α-D-gentiobiosyl-1′,2′-orthoacetate);
1α-(α-D-glucopyranosyl-1′,2′-orthoacetate)-Vitamin $D_3$;
1α-(α-D-cellobiosyl-1′,2′-orthoacetate)-Vitamin $D_3$.

All of the aforementioned derivatives can also be prepared with Vitamin $D_2$.

The derivatives of Vitamins D of the present invention can be prepared by standard synthetic methods well known to those skilled in the art. These methods depend on whether the starting Vitamin $D_3$ or Vitamin $D_2$ contains one or more hydroxy groups. When the vitamin contains only one hydroxy group, the syntheses are straightforward, since the monohydroxylated Vitamin D (hydroxylated at position 3) is treated with silver trifluoromethanesulphonate (triflate) and the proton acceptor 2,4,6-trimethylpyridine (collidine) in an inert solvent such as dichloromethane, benzene or toluene, to which is added a fully acylated glycoside or fully acylated straight or branched chain glycosidic polymer, either of these containing an appropriate leaving group (L.G.) at position C-1' of the terminal ring (or on the single ring, as called for). Condensation occurs according to the following reaction, indicated here for a single glycosyl orthoester for the purpose of illustration only:

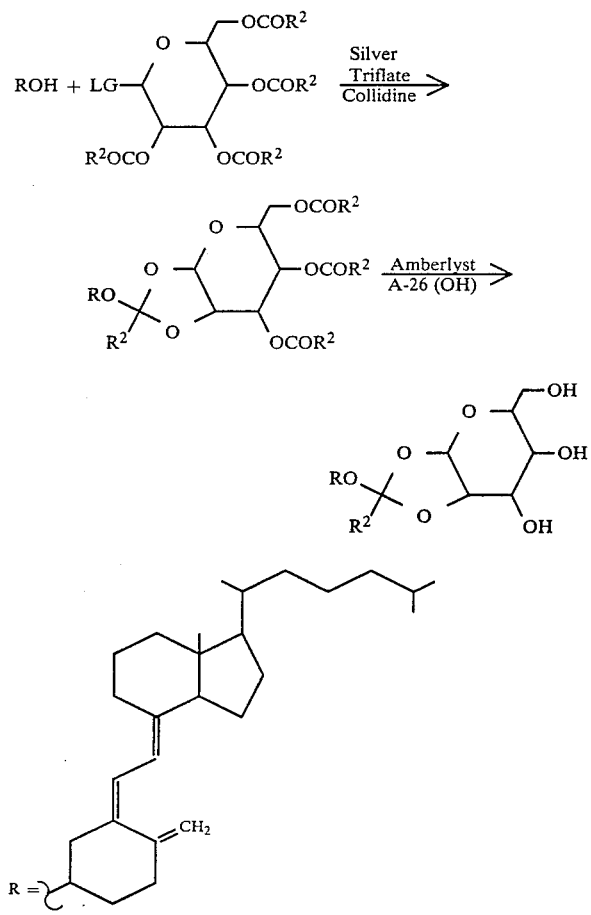

In this reaction sequence, $R^2$ is as defined previously, LG is a common leaving group such as bromine, chlorine, iodine, p-toluenesulfonyl, and the like, capable of being replaced in a bimolecular nucleophilic substitution reaction.

When the Vitamin $D_3$ or $D_2$ is reacted with a glycosidic polymer, one or more of the $OCOR^2$ groups in the glycopyranoside or glycofuranoside rings is replaced by a fully acylated glycosidic unit, with the proviso that the total number of glycosidic units not exceed 100, preferably 20.

The reaction is carried out at from $-70°$ C. to room temperature or above for a period of 1–10 hours, and is thereafter cooled and filtered to remove the silver salt. The filtrate is dried and the inert solvent is evaporated. The resulting product can be purified by any of the standard modern purification methods such as high performance liquid chromatography, silicic acid chromatography, thin layer preparative chromatography, and the like.

After separation of the individual products, the glycosidic residues are deacylated in base, such as with a strong base ion exchange resin, such as Amberlyst A-26(OH). Further purification by high performance chromatography is usually indicated to obtain the highly purified product.

When the starting Vitamin D ($D_3$ or $D_2$) carries two hydroxy groups (such as in 1-hydroxy Vitamin $D_3$, or 25-hydroxy Vitamin $D_3$) one of these may need to be selectively protected with a protecting group which can be ultimately removed after the condensation, and before, during and after the deacylation of the glycosidic residues. The same is true if three or more hydroxy groups are present in the vitamin starting materials, and less than all of these require to be glycosylated.

The selective protection of hydroxy groups in the starting materials can be carried out by using standard protection and deprotection reactions, well known to those skilled in organic chemistry.

Because each of the hydroxyl groups on the Vitamin D molecule have different reactivities either due to the fact that they are either primary (e.g., 26-OH), secondary (e.g., 24-OH), 3β-OH, etc.) or tertiary (e.g., 25-OH) hydroxyl functions, selectivity can be achieved. Furthermore, because of steric considerations the 3β-OH has different reactivity than the 1 —OH which is both a vicinyl hydroxyl function as well as sterically hindered by the exocyclic $C_{19}$ methylene function on $C_{10}$. A good example of these reactivities is illustrated in Holick et al., *Biochemistry:* 10, 2799, 1971, where it is shown that the trimethylsilyl ether derivative of 1,25-$(OH)_2$-$D_3$ can be hydrolyzed in HCl—MeOH under mild conditions to yield 3,25-disilyl ether, and 25-monosilyl ether derivatives of 1,25-$(OH)_2$-$D_3$. Furthermore, to obtain a 1,25-$(OH)_2$-$D_3$ whereby the 3 and 1 hydroxyls are protected, the 25-monosilyl ether derivative of 1,25-$(OH)_2$-$D_3$ can be acetylated to form the 1,25-(OH)-2-$D_3$-1,3-diacetyl-25-trimethyl silyl ether. Because the acetates are quite stable to acid hydrolysis, this derivative can be acid hydrolyzed to yield 1,3-diacetoxy-25-hydroxyvitamin $D_3$. An alternative approach would simply be to acetylate 1,25-$(OH)_2$-$D_3$ in acetic anhydride in pyridine at room temperature for 24 to 48 h. to yield 1,3-diacetoxy-25-hydroxyvitamin $D_3$.

For protecting the 25-hydroxyl group for 25-hydroxyvitamin $D_3$ the following can be done: 25-OH-$D_3$ can be completely acetylated in acetic anhydride and pyridine under refluxing conditions for 24 h. The 3-Ac can be selectively removed by saponification (KOH in 95% MeOH-water) at room temperature for 12 h.

Once the desired protected Vitamin D derivative is prepared, the same is reacted with silver triflate and collidine or other methods for coupling (as described e.g. by Igarashi, K., in *Advances in Carbohydrate Chemistry and Biochemistry,*" Vol. 34, 243–283, or Banoub, J., *Can. J. Chem.,* 57: 2091–2097 (1979), and the glycosidic or polyglycosidic residue as in scheme I above, followed by deacylation, deprotection and purification. Among the starting vitamin D derivatives which are readily available, are, for example:

Vitamin $D_3$;
Vitamin $D_2$;
1-hydroxy-Vitamin $D_3$;
1-hydroxy-Vitamin $D_2$;
25-OH-Vitamin $D_3$;

25-OH-Vitamin $D_2$;
1,24-$(OH)_2$-Vitamin $D_3$;
1,25-dihydroxy-Vitamin $D_3$;
1,25-dihydroxy-Vitamin $D_2$;
24,25-dihydroxy-Vitamin $D_3$;
25,26-dihydroxy-Vitamin $D_3$;
24,25-dihydroxy-Vitamin $D_2$;
1,24,25-trihydroxy-Vitamin $D_3$;
1,25,26-trihydroxy-Vitamin $D_3$.

Some materials, such as 25,26-Vitamin $D_2$, 1,24,25-trihydroxy Vitamin $D_2$ or 1,25,26-trihydroxy Vitamin $D_2$ have not yet been fully identified in the art, but can nevertheless be used if synthetically prepared.

The acylated glycoside containing a leaving group at position C-1' of the first (or only) glycosidic ring can be prepared, for example, by the methods of Fletcher, H. G., Jr., *Methods in Carbohydrate Chemistry* 2: 228 (1963), or Bonner, W. A., *Journal of Organic Chemistry* 26: 908–911 (1961), or Lemieux, R. U., *Methods in Carbohydrate Chemistry*, Vol. II, 221–222.

The 26,26,26,27,27,27 hexafluoro, 1α,25 dihydroxy Vitamin $D_3$ can be made according to the method of De Luca et al., Belgium BE No. 896,830.

Oligosaccharide intermediates can be prepared, for example, by the methods of Lemieux, R. U., *J. of Amer. Chem. Soc.* 97: 4063–4069 (1975); or Frechet, J. M. J., *Polymer-Supported Reactions in Organic Synthesis* (1980) 407–434, or Kennedy, J. F., *Carbohydrate Chemistry* 7:496–585 (1975).

Commercially available sugars include (Pfanstiehl Laboratories, Inc.): Pentoses, such as: D-Arabinose, L-Arabinose, D-Lyxose, L-Lyxose, D-Ribose, D-Xylose, L-Xylose; Hexoses, such as: Dextroses, D-Fructose, D-Galactose, α-D-Glucose, β-D-Glucose, L-Glucose, Levulose, D-Mannose, L-Mannose, L-Sorbose; Heptoses, such as: D-Glucoheptose, D-Mannoheptulose, Sedoheptulosan; Disaccharides, such as: Cellobiose, 3-O-β-D-Galactopyranosyl-D-arabinose, Gentiobiose, Lactoses, α-Lactulose, Maltose, α-Melibiose, Sucrose, Trehalose, Turanose; Trisaccharides, such as: Melezitose, Raffinose; Tetrasaccharides, such as: Stachyose; Polysaccharides and derivatives, such as: Arabic Acid, Chitin, Chitosan, Dextrin, Cyclo-Dextrins, Glycogen, and Inulin.

Alternatively, the whole synthetic sequence (protection, condensation and deprotection) can be carried out starting with a $\Delta^{5,7}$ steroidal diene which is a provitamin D of any D compound. After orthoesterification, the provitamin is ring-opened photochemically, and the resulting previtamin is thermally rear-ranged to yield orthoesterified vitamin.

It is known (Napoli, J. L. and DeLuca, H. F., in *Burger's Medicinal Chemistry* 4th Ed., part II, page 728 ff) that the active form of Vitamin D is 1,25-dihydroxy-Vitamin $D_3$. When 1,25-dihydroxy-Vitamin $D_3$ orthoester is used in the treatment of hypocalcemic states, or in the regulation of phosphorus and calcium metabolism in an animal, especially in a human, endogenous hydrolysis, some of which by enzymes of the animal, directly release the active form of the vitamin. On the other hand, when non-hydroxylated derivatives of the vitamin are used (such as, e.g., Vitamin $D_3$ orthoester), release of the hydroxylated vitamin is followed by hydroxylation in the liver and then in the kidney in order to form the active 1,25-dihydroxy Vitamin.

The water-soluble Vitamin D conjugates of the present invention include hydrophilic derivatives of good water solubility to derivatives of excellent water solubility. They can be used generally in any application where the use of Vitamin $D_3$, Vitamin $D_2$ or hydroxylated derivatives thereof has been called for in the prior art. The advantage of the conjugates of the invention resides in their water-solubility and thus their ease of administration in aqueous media such as, for example, saline or aqueous buffers. This allows the utilization of these conjugates in such devices as Vitamin D releasing in-line pumps, intravenous dispensation and the like. Other advantages include treatment of fat malabsorption syndromes, as well as release of the biologically active form of Vitamin $D_3$ in the gut, e.g. 1,25-$(OH)_2$-$D_3$ glycosyl orthoester→gut→1,25$(OH)_2$-$D_3$→biological action.

The conjugates of the invention can be administered by any means that effect the regulation of calcium and phosphorus homeostasis and metabolism in animals, especially humans. For example, administration can be topical, parenteral, subcutaneous, intradermal, intravenous, intramuscular, or intraperitoneal. Alternatively, or concurrently, administration can be by the oral route. The dosage administered will be dependent upon the age, health and weight of the recipient, kind of concurrent treatment if any, frequency of treatment, and the nature of the effect desired. Generally, from 0.01 μg to 10 μg per kg per application, in one or more applications per therapy, is effective to obtain the desired result.

An additional, unexpected property of the compounds of the invention is that some of them may demonstrate promotion of calcium absorption through the intestine without effecting calcium mobilization brought about by calcium release from bones. Calcium mobilization by bone release is a common feature of 1,25-dihydroxy vitamin $D_3$. Its selective absence in some of the compounds of the invention has a beneficial therapeutic consequence by promoting an increase in serum calcium levels by stimulating intestinal calcium transport. It is disadvantageous for patients with severe bone disease to maintain serum calcium levels at the expense of mobilizing calcium from their wasting bones.

The compounds can be employed in dosage forms such as tablets, capsules, powder packets or liquid solutions, suspensions or elixirs for oral administration, or sterile liquids for formulations such as solutions or suspensions for parenteral use. In such compositions, the active ingredient will ordinarily always be present in an amount of at least $1 \times 10^{-6}\%$ by wt. based upon the total weight of a composition, and not more than 90% by wt. An inert pharmaceutically acceptable carrier is preferably used. Among such carriers are 95% ethanol, vegetable oils, propylene glycols, saline buffers, etc.

Having now generally described this invention, a more complete understanding can be obtained by reference to certain examples, which are included herein for purposes of illustration only and are not intended to be limiting unless otherwise specified.

EXAMPLE 1

Preparation of Vitamin $D_3$, α-D-glucopyranosyl-1',2'orthoacetate

Reaction of Vitamin $D_3$ with Acetobromoglucose

To a solution of Vitamin $D_3$ (38.5 mg., 0.100 mmole) in dry $CH_2Cl_2$ (2 ml) was added silver trifluoromethanesulphonate (56.5 mg, 0.220 mmole), 2,4,6-trimethylpyridine (30 μl, 0.227 mmole), and a solution of acetobromoglucose (80.3 mg, 0.195 mmole) in CH₂Cl₂ (3 ml). After stirring in the dark under N₂ for 2 h. at 0° and then 4 h. at room temperature, the suspension was diluted with CH₂Cl₂ and filtered through Celite. The filtrate was washed successively with H₂O, 0.1M H₂SO₄, saturated KHCO₃, and H₂O and then co-evaporated with 100% EtOH under N₂. The resulting oil was purified by preparative thin-layer chromatography using 20% EtOAc in hexane, giving 25.2 mg (35.2%) of Vitamin D₃ 3',4',6'-tri-O-acetyl-α-D-glucopyranosyl-1',2'-orthoacetate ($R_f$ 0.28). Its UV spectrum in CH₃OH had an absorbance maximum of 265 nm and an absorbance minimum of 228 nm, characteristic of the 5,6-cis-triene chromophore in Vitamin D. Its mass spectrum exhibited a peak for the parent molecular ion at m/e 714. Its ¹HMR spectrum (CDCl₃) showed the signal for H-1' as a doublet at 5.70 with a coupling constant of 5.12 Hz. Other characteristic ¹HMR signals are as follows: 0.54 (s, 3H, Me-18); 0.86 and 0.88 (2s, 6H, Me₂-26,27); 0.92 (d, 3H, J 5.92 Hz, Me-21); 1.76 (s, 3H, C—CH₃); 2.10, 2.12, 2.14 (3s, 9H, AcO-); 4.35 (m, 1H, H-3); 3.81–5.20 (m, 6H, H-2', H-3', H-4', H-5', 2H-6'); 4.81 (bs, 1H, H-19); 5.03 (bs, 1H, H-19); 6.01 and 6.21 (AB$_{quasi}$, 2H, J 11.12 Hz, H-6,7).

Deacetylation

The strong base ion-exchange resin, Amberlyst A-26 (OH), obtained by treating Amberlyst A-26 with NaOH soln., was used for deacetylation because it avoids the problem of removing ionic salts (which accompany deacetylation) from a water-soluble product. A mixture of Vitamin D₃ 3',4',6'-tri-O-acetyl-α-D-glucopyranosyl-1',2'-orthoacetate (35.2 mg, 0.0492 mmole) and Amberlyst A-26 (OH) (185 mg) in 15 ml of CH₃OH was refluxed under N₂ for 4 h. The resin beads were filtered off, and the filtrate was concentrated under N₂. The resulting oil was purified by preparative thin-layer chromatography using 5% hexane in ethyl acetate, giving 22.5 mg (83.5%) of the product ($R_f$ 0.5). The UV spectrum of Vitamin D₃α-D-glucopyranosyl-1',2'-orthoacetate, had $\lambda_{max}$ 265 nm and $\lambda_{min}$ 228 nm. The ¹HMR signal for H-1' was a doublet at δ 5.67 with a coupling constant of 5.63 Hz. Other ¹HMR signals (CD₃OD) include: δ 0.55 (s, 3H, Me-18); 0.86 and 0.89 (2s, 6H, Me₂-26,27); 0.94 (d, 3H, J 6.14, Me-21); 1.68 (s, 3H, C—CH₃); 3.30–3.87 (m, 6H,H-2',H-3',H-4',H-5',2H-6'); 4.25 (m, 1H, H-3); 4.74 (d, 1H, J 1.4 Hz, H-1'9); 5.03 (bs, 1H, H-19); 6.03 and 6.21 (AB$_{quasi}$, 2H, J 11.00 Hz, H-6,7).

The Vitamin D₃,α-D-glucopyranosyl-1',2'-orthoacetate and the 25 OH derivative were tested for biological activity. Male weanling rats from Holtzmann Company, Madison, Wisc., U.S.A., were fed a Vitamin D deficient diet that was adequate in phosphorus and low in calcium (0.02%) for 3½ weeks. Groups of five animals received orally either 0.25 μg in 50 μl of 95% ethanol, or vehicle alone. 24 hours later the animals were sacrificed and the small intestine and blood were collected. Intestinal calcium transport studies were performed by the everted gut sac technique, and blood was used for serum calcium determinations.

The results are shown in the following Table 1:

TABLE 1

| Compound | BIOASSAY | |
|---|---|---|
| | I/O | Serum Calcium |
| Control | 1.7 ± 0.12 | 4.7 ± 0.1 |
| Vitamin D₃ (325 pmoles) | 3.3 ± 0.2 | 5.7 ± 0.16 |
| Vitamin D₃-α-D-glucopyranosyl- | 3.0 ± 0.2 | 5.0 ± 0.1 |

TABLE 1-continued

| Compound | BIOASSAY | |
|---|---|---|
| | I/O | Serum Calcium |
| 1',2'-orthoacetate (325 pmoles) | | |
| 25-OH—D₃-α-D-glucopyranosyl-1',2'-orthoacetate (325 pmoles) | 3.7 ± 0.1 | 6.6 ± 0.2 |

What is claimed is:

1. A compound selected from the group consisting of formula (IA) and (IB):

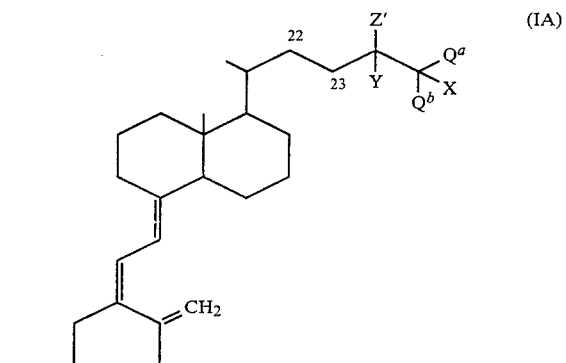

(IA)

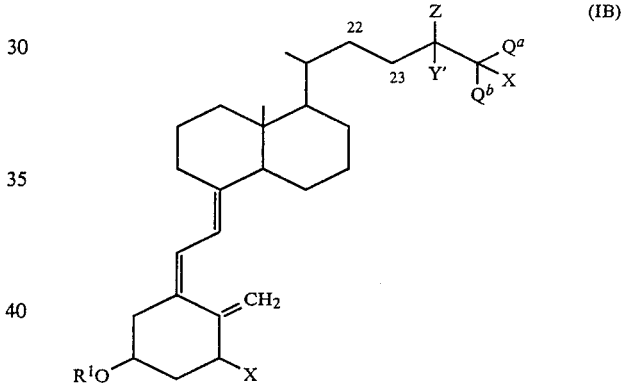

(IB)

wherein the bond between carbons C-22 and C-23 is single or double;

Y is hydrogen, F, —CH₃ or —CH₂CH₃;

Z is F, H or X;

Y' is H, —CH₃ or —CH₂CH₃;

Z' is F or H;

$Q^a$ is CF₃ or CH₂X;

$Q^b$ is CF₃ or CH₃;

X is selected from the group consisting of hydrogen and OR¹, where R¹ is hydrogen or an orthoester glycoside moiety of the formula (II)

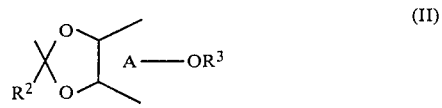

(II)

where A represents a glucofuranosyl or glucopyranosyl ring; R² is hydrogen, lower alkyl, aralkyl, or aryl; and R³ is hydrogen or a straight or branched chain glycosidic residue containing 1–100 glycosidic units per residue;

with the proviso that at least one said R¹ is an orthoester glycoside radical of formula (II).

2. The compound of claim 1 wherein the bond at position C-3 is β.

3. The compound of claim 1 wherein, when X at position C-1 is —OR¹, the bond at C-1 is α.

4. The compound of claim 1 wherein R³ is a glycosidic residue having 1–10 units per residue.

5. The compound of claim 4, wherein said glycosidic residue has 1, 2 or 3 glycosidic units per residue.

6. The compound of claim 1 wherein the bond between C-22 and C-23 is single, and Y=H.

7. The compound of claim 6 wherein said compound contains one orthoester glycoside residue.

8. The compound of claim 5 wherein said glycosidic residue R³ contains 2 glycosidic units.

9. The compound of claim 5 wherein said glycosidic residue R³ contains 3 glycosidic units.

10. The compound of claim 1 which is

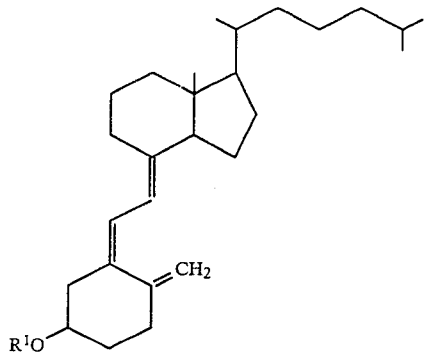

wherein R¹ is said orthoester moiety of formula (II).

11. The compound of claim 10 wherein, in said orthoester moiety, said glycosidic residue R³ has 1, 2 or 3 glycosidic units.

12. The compound of claim 1 which is

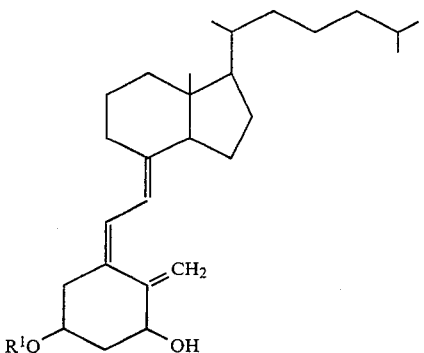

wherein R¹ is said orthoester moiety of formula (II).

13. The compound of claim 12 wherein in said orthoester moiety said glycosidic residue R³ has 1, 2 or 3 glycosidic units.

14. The compound of claim 1 which is

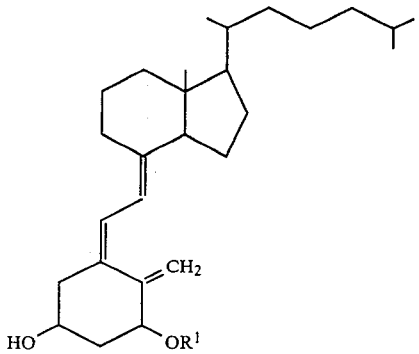

wherein R¹ is said orthoester moiety of formula (II).

15. The compound of claim 14 wherein, in said orthoester moiety residue, said glycosidic residue R³ has 1, 2 or 3 glycosidic units.

16. The compound of claim 1 which is

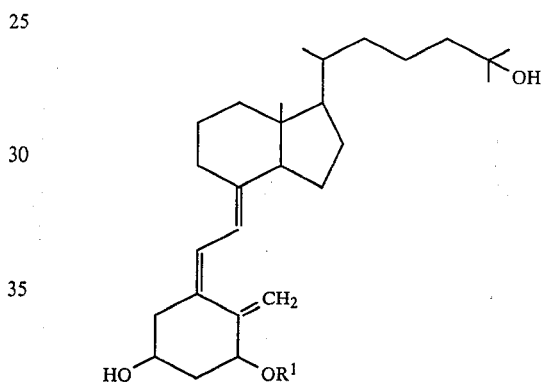

wherein R¹ is said orthoester moiety of formula (II).

17. The compound of claim 16 wherein, in said orthoester moiety, said residue R3 contains 1, 2 or 3 glycosidic units.

18. The compound of claim 1 which is

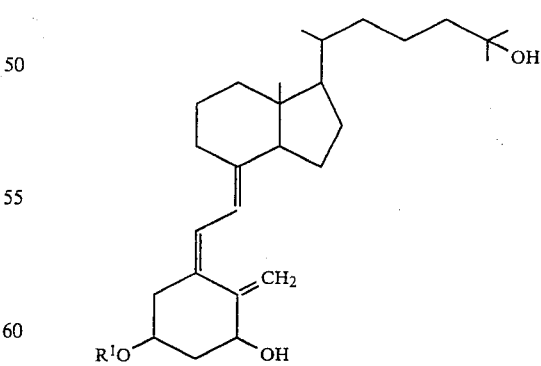

wherein R¹ is said orthoester moiety of formula (II).

19. The compound of claim 18 wherein, in said orthoester moiety, said glycosidic residue R3 contains 1, 2 or 3 glycosidic units.

20. The compound of claim 1 which is

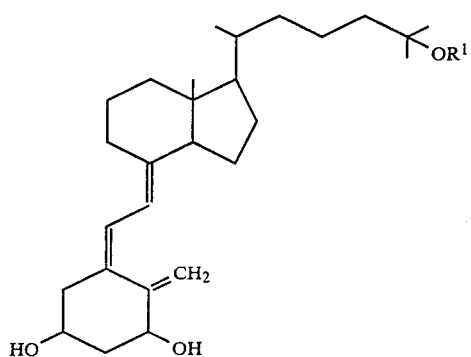

wherein $R^1$ is said orthoester moiety of formula (II).

21. The compound of claim 20 wherein in said orthoester moiety, said glycosidic residue $R^3$ has 1, 2 or 3 glycosidic units.

22. The compound of claim 1 which is

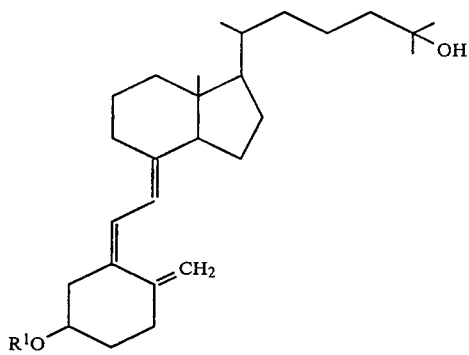

wherein $R^1$ is a said orthoester moiety of formula (II).

23. The compound of claim 22 wherein, in said orthoester moiety, said glycosidic residue contains 1, 2 or 3 glycosidic units.

24. The compound of claim 1 which is

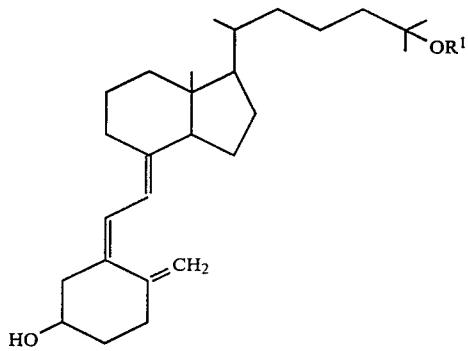

wherein $R^1$ is said orthoester moiety of formula (II).

25. The compound of claim 24 wherein, in said orthoester moiety, said glycosidic residue $R^3$ contains 1, 2 or 3 glycosidic units.

26. The compound of claim 1 which is

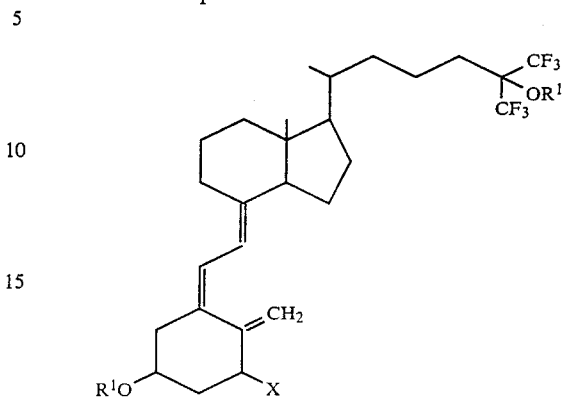

wherein $R^1$ is said orthoester moiety of formula II.

27. The compound of claim 26 which is

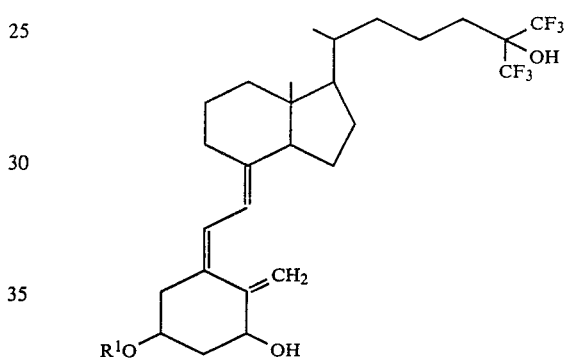

wherein $R^1$ is said orthoester moiety of formula II.

28. The compound of claim 26, which is

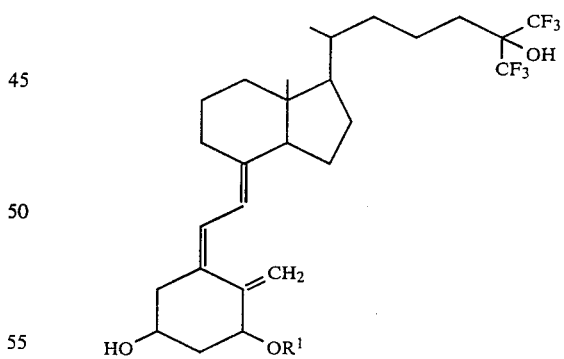

wherein $R^1$ is said orthoester miety of formula II.

29. A method of treating calcium metabolic disorders in an animal which comprises administering to said animal an amount sufficient to regular calcium and phosphorous homeostasis in said animal, of a compound of any of claims 1, or 10–28.

* * * * *